United States Patent [19]
Lech

[11] Patent Number: 6,027,746
[45] Date of Patent: Feb. 22, 2000

[54] CHEWABLE SOFT GELATIN-ENCAPSULATED PHARMACEUTICAL ADSORBATES

[75] Inventor: Stanley Lech, Rockaway, N.J.

[73] Assignee: Warner-Lambert Company, Morris Plains, N.J.

[21] Appl. No.: 09/064,324

[22] Filed: Apr. 22, 1998

Related U.S. Application Data
[60] Provisional application No. 60/044,098, Apr. 23, 1997.

[51] Int. Cl.⁷ .................................................. A61K 9/48
[52] U.S. Cl. ........................ 424/455; 424/452; 424/456; 424/683; 514/962; 514/974
[58] Field of Search ..................................... 424/451, 452, 424/455, 456, 439, 683; 514/962, 974

[56] References Cited

U.S. PATENT DOCUMENTS

| | | | |
|---|---|---|---|
| 3,567,819 | 3/1971 | Idson et al. | 424/441 |
| 4,428,927 | 1/1984 | Ebert et al. | 424/440 |
| 4,532,126 | 7/1985 | Ebert et al. | 427/2.18 |
| 4,632,821 | 12/1986 | Peters et al. | 424/490 |
| 4,647,459 | 3/1987 | Peters et al. | 424/683 |
| 4,650,663 | 3/1987 | Peters et al. | 424/484 |
| 5,112,604 | 5/1992 | Beurline et al. . | |
| 5,229,137 | 7/1993 | Wolfe | 424/687 |
| 5,244,670 | 9/1993 | Upson et al. | 424/439 |
| 5,817,323 | 10/1998 | Hutchinson et al. | 424/439 |
| 5,891,801 | 4/1999 | Calam et al. | 424/195.1 |
| 5,908,636 | 6/1999 | Devlin et al. | 424/452 |
| 5,916,590 | 6/1999 | Cody et al. | 424/452 |
| 5,919,481 | 7/1999 | Cody et al. | 424/452 |

FOREIGN PATENT DOCUMENTS 1388786  3/1975  United Kingdom .

*Primary Examiner*—Robert H. Harrison
*Attorney, Agent, or Firm*—Michael J. Atkins; Evan J. Federman

[57] ABSTRACT

The present invention relates to novel liquid oral suspensions incorporated within a soft gelatin capsule comprised of a bitter or bad-tasting pharmaceutical active (such as antihistamines, decongestants and the like) which is dispersed within an adsorbate comprised of magnesium trisilicate, silicon dioxide or mixture thereof. The adsorbate is dispersed within an aqueous or non-aqueous carrier base and combined with other flavors, sweeteners, emulsifiers and the like. The adsorbate not only taste-masks the active but also insures that is evenly dispersed through the liquid suspension so that a uniform dosage rate is readily achievable. The encapsulation of the adsorbate within a gelatin capsule makes administration easier for children andmore convenient. The capsule also affords the adsorbate suspension greater shelf life.

15 Claims, No Drawings

CHEWABLE SOFT GELATIN-ENCAPSULATED PHARMACEUTICAL ADSORBATES

This application claims the benefit of U.S. Provisional No. 60/044,098 filed Apr. 23, 1997.

FIELD OF THE INVENTION

The present invention relates generally to pharmaceutical delivery systems for the oral administration of therapeutic drugs. More specifically, the invention relates to delivery systems for the oral administration of bitter or otherwise unpleasant tasting drugs in a manner that is more palatable and less objectionable to young children and some older patients as well.

BACKGROUND OF THE INVENTION

There are many means in which therapeutic agents can be administered to a patient such a intravenous, intramuscular or intraperitoneal injections, naso-gastric tubes, transdermal patches and the like. Oral delivery systems have proven to be the easiest means for drug administration when the active can be absorbed into the digestive system as the tablet or oral suspension containing the drug of interest can be simply placed in the mouth and swallowed with or without water. Oral delivery also provides a relatively fast and efficient means to get the drug absorbed into the digestive system and dissolved into the bloodstream where the active drug is delivered to wherever necessary.

There have been numerous pharmaceutical vehicles developed over the years for the oral administration of drugs and therapeutic agents. Oral delivery systems have consisted of solid tablets that must be swallowed whole; solid tablets that dissolve in water and are then consumed; confectionery delivery systems in which the pharmaceutical agent is provided in a flavored, pleasant-tasting vehicle which is either chewed and ingested or is allowed to dissolve slowly in the mouth. The drug may also be dissolved and suspended in a liquid vehicle such as a flavored cough syrup which is easily swallowed.

One of the drawbacks to oral delivery systems however, is the situation wherein the drug to be administered is bitter, bad-tasting, odorous or in some manner organoleptically unpleasant. Many efforts have been made in the past to "taste mask" these compounds either through elaborate flavor and/or sweetener delivery systems, adsorption of the drug within another material or by encapsulation with a polymer, fat, carbohydrate or other like material. These taste-masking methods basically prevent the bitter tasting components of the drug from contacting the taste-buds during oral ingestion yet break down and release the active upon dissolution in the stomach. However, each of these methods also have their own drawbacks and the search remains for a fast-acting, non-offensive easily administrable oral drug delivery system.

U.S. Pat. No. 4,632,821 to Peters et al. discloses a medicament adsorbate in which a pharmaceutical such as an anti-tussive, antihistamine, decongestant and the like is adsorbed onto magnesium trisilicate particles having a flake-like structure and a surface area of at least 400 $m^2/g$. Whereas a number of pharmaceutical compositions are listed as being useful in the practice of the present invention, decongestants are the active of choice and are preferably formulated as a chewing gum or lozenge.

U.S. Pat. No. 4,647,459 also to Peters et al. discloses and claims a confectionery composition in which a pharmaceutical active is dispersed within a magnesium trisilicate adsorbate. The adsorbate is incorporated in a lozenge, tablet, toffee or nougat in an amount of from about 1.0% t 20% by weight.

U.S. Pat. No. 5,112,604 to Beurline et al. discloses an oral pharmaceutical liquid suspension comprised of theophylline as the active agent, silicon dioxide, a wetting agent and a hydrocolloid gum. The gum and silicon dioxide act to suspend the agent evenly throughout the liquid thereby insuring uniform dose dispersions. Whereas theophylline is the primary drug of interest anti-inflammatories, analgesics, antihistamines and others are also listed as suitable for use with the invention.

U.S. Pat. No. 4,650,663 also to Peters et al. discloses the preparation of an oral pharmaceutical delivery system in which an unpleasant tasting anti-tussive such as noscapine, carbetapentane citrate or clophedianol hydrochloride is adsorbed onto magnesium silicate flakes and incorporated into a chewable tablet or lozenge. The adsorbate allegedly masks the bitter taste to an almost negligible level to encourage better patient compliance.

U.K. Patent 1,388,786 assigned to the Schereer Corporation discloses an integral solid dosage carrier for pharmaceutical agents consisting of a gel-lattice structure that has been extruded into conventional configurations. The gel lattice consists of water-soluble colloidal hydrates such as gelatin, derivatives. The drug of interest is dissolved and mixed in the hydrate which is in liquid form. A plasticizer such as glycerin or triethyl citrate is then added which causes the gel lattice to form. Since it is relatively rigid containing from only 15%–20% water, no outer coating is needed for the dosage forms to retain their form and solubility over time.

It is an object of the present invention to provide a novel, oral delivery system that is chewable for rapid release of the active yet is pleasant tasting even when bitter tasting or otherwise unpalatable drug actives are involved. The drug is dispersed within an oral suspension comprising a medicament adsorbate and is then incorporated within a gelatin capsule. The soft, chewable capsules will encourage better patient compliance in difficult patients such as young children who are hesitant to swallow pills, caplets or capsules. The dosage form also provides excellent stability for the drug for extended longer term shelf life.

SUMMARY OF THE INVENTION

A novel pharmaceutical delivery system is comprised of a chewy, soft gelatin capsule within which a drug adsorbate is dispersed in a solid or liquid fill material. The drug is absorbed onto flake-like particles of an adsorbate such as magnesium trisilicate, silicate dioxide or preferably a mixture of both. The fill material of the capsule within which the adsorbate is dispersed is comprised of flavors, sweeteners, corn syrup, solvents and other food-grade excipient that assist in the stabilizing and taste-masking of bitter tasting drugs.

DETAILED DESCRIPTION OF THE INVENTION

Chewable tablets and capsules are highly valuable forms of oral pharmaceutical delivery systems in both the prescription and over the counter markets due to the convenience of their administration; i.e., no water is necessary. However, the bitter or unpalatable tastes of most drugs has severely limited their acceptance in these markets. The present invention seeks to overcome these limitations by affording a chewable gelatin capsule in which the bitter taste of the drug has been masked through the use of a drug adsorbate disposed therein together with other pleasant tasting syrup carriers, flavors, sweeteners and the like.

The adsorbate suspension technology of the present invention that is incorporated within the gelatin capsule is comprised of a pharmaceutical active adsorbed onto a magnesium trisilicate microgranule or agglomerate. The drug/adsorbate composition is dispersed in an aqueous or non-aqueous carrier solvent which is then injected into a chewable gelatin capsule so the drug can be ingested and readily adsorbed into the patient's stomach for quick relief. With magnesium trisilicate adsorbate technology, the present invention can provide chewable encapsulated liquid suspensions that would otherwise be bitter tasting, with superior taste to other drug delivery systems known in the art. Moreover, despite the presence of the solid adsorbate, there is no gritty texture due to the preparation of the adsorbate in a very small particle size. The gelatin capsules known in the art generally must be swallowed whole which again is a problem for children, the elderly and others who have difficulty in swallowing.

Magnesium trisilicate ($Mg(O_3S)_3$) is a fine, white odorless and tasteless powder that is a well known adsorbent, antioxidant and antacid. The compound is an excellent adsorbate carrier for pharmaceutical agents as it can form flake-like lattice structures with many interstitial spaces that provides a large surface area for maximum drug loading. When solubilized in an aqueous-solution containing the drug of interest, the flakes can then be precipitated as masses with the drug adsorbed within the interstitial crevices between the individual flakes. The drug adsorbate is then mixed within the carrier fill which is encapsulated by the soft gelatin capsule.

Silicon dioxide, ($SiO_2$) or silica is a second substance useful as the adsorbate for the active agent in the practice of the present invention. A colorless crystalline powder, it also may be precipitated from solution as clumped flakes with interstitial spaces in which the active pharmaceutical is trapped and adsorbed. Preferably, the adsorbate used in the practice of the present invention is comprised of a mixture of both magnesium trisilicate and silicon dioxide in a 1:1 ratio.

The pharmaceutical agent useful in the delivery system of the present invention could conceivably be any active drug capable of delivery by oral administration. For example, suitable pharmaceuticals might include anti-tussives, antacids, analgesics, antihistamines, anti-arrythimics, decongestants, anti-inflammatory agents, central nervous system drugs, diuretics, antidiarrheal compounds, steroids, antibiotics, chemotherapeutic agents, neoplastic agents, antiparasitic agents and the like. The only criteria as to whether the drug would be useful in the chewable delivery system is whether it can provide its therapeutic effect after ingestion and absorbation and its compatibility with the filler material and chewable gelatin shell. Other criteria to consider is the drug's dissolution rate and shelf life stability.

Conceivably the, the specific therapeutic agent useful in the practice of the present invention can be any one of the many pharmaceutical agents that may be delivered orally, ingested, and then absorbed through the digestive tract and into the bloodstream. Preferably however, the drug active is both water soluble and one of the many unpleasant tasting drugs currently available on the Rx and over the counter market. Pharmaceutical actives of this type include antitussive compounds such as dextromethorphan, detromethorphan hydrobromide, noscapine, carbetapentane citrate, chlorphedianol hydrochloride and the like; sedating antihistamines include chlorphenramine, phenidamine, doxylamine, phenylOxamine, diphenhydramine, promethazine and triprolidine, hydroxyzine, meclinzine, cyproheptadine, azatadine their salts and mixtures thereof. Suitable non-sedating antihistamines include fexofenadine, terfenadine, astemizole, loratadine and cetirizine, while suitable decongestants include phenylephrine, phenylpropanolamine, pseudoephedrine, ephedrine, theirs salts and mixtures thereof.

Nonsteroidal anti-inflammatory agents (NSAIDS) may also be incorporated in the absorbate compositions of the present invention. Suitable NSAIDS include ibuprofen, ketoprofen, acetylsalicylic acid, ketoprofen, aproxen, naprosyn, meclomen, indomethicin and mixtures thereof. Suitable analgesics include acetaminophine. $H^2$-antagonists useful in the composition of the present invention include famotidine, ranitidine, cimetidine and mixtures thereof.

Useful antibiotics, antibacterials and bactericidals include erythromycin, cephalosporin, tetracyclines, penicillin, amoxycillin, clathromycin and mixtures thereof. Useful anti-convulsants include phenyltoin and thosuximide.

The wide variety of pharmaceuticals useful herein include their acid addition salts. Both organic and inorganic salts may be used and exemplary acid salts include the hydrochloride, hydrobromide, orthophosphate, benzoate, maleate, tartrate, succinate, citrate, salicylate sulfate, acetate and mixtures thereof.

The pharmaceutical or therapeutic agent is preferably first dissolved in water or some other organic solvent for those drugs which are not water soluble. Depending on the dosage desired, and the type of drug involved, the drug is added in an amount of from 0.5% to about 25% w/w of the absorbate. Once complete dissolution of the active has occurred, the solution is added to the absorbate in amounts of from about 0.1 to about 3.0 mls. per gram of absorbate. The preferred absorbate for the use in the practice of the present invention is magnesium trisilicate ($2MgO_3SiO_2H_2O$) or silicon dioxide ($SiO_2$) and most preferably a combination of the two. The magnesium trisilicate and silicon dioxide are very fine, white, odorless powders with flake-like structures with multiple interstitial spaces.

Once the pharmaceutical solution is prepared, it is added to the magnesium trisilicate/silicon dioxide powder and a slurry is prepared as the absorbate and drug are combined. The absorbate/drug carrier agent is then dispersed into a non-aqueous or aqueous base using a moderate to high sheer mixer.

Suitable non-aqueous bases may be selected from the group comprising vegetable oils and fats, animal fat, mineral oils, paraffin and wax, natural fatty acids any edible oil, glycerin, sugar and mixtures thereof. Suitable aqueous-based solvents include water with a second excipient comprised of sorbitol, glycerine, corn syrup, sugar, alcohols and mixtures thereof.

Again, the amount of pharmaceutical active incorporated into the magnesium/silicate will vary depending on the target dosage and the type of drug to be taste masked. Generally, the active will be mixed in amounts of from 0.2 grams to about 0.3 grams per gram of absorbate. The amount of active absorbate per volume of liquid carrier will also vary but generally may be from about 1.0% to about 15% active/adsorbate based on the total weight percent (wt %) of the liquid formulation.

The filler composition that carries the adsorbate within the soft chewable shell is comprised of flavors, sweeteners, colorants, solvents, preservatives, polyethylene glycol, corn syrup, emulsifiers, gums/thickeners, oils and fat fillers and other insoluble or soluble excipients. The specific components of each genus can be readily ascertained by those skilled in the art. Flavor and component compatibility are perhaps the major criteria in the excipient selection.

In formulating the final suspension product, additional excipients such as flavoring agents, preservatives, gums/thickeners, sweeteners, coloring agents, emulsifiers, fillers, oils and fats and the like may be added to the encapsulated oral suspension to further improve the taste and palatability thereof during chewing. These can be added in varying amounts as is known in the art and as desired according to the formulation. Generally, a standard liquid will be comprised of the following components in their respective amounts, based on the total weight percent of the liquid suspension.

| Compositions | Percentage |
| --- | --- |
| Drug adsorbate | 1.00–15.00% |
| Sorbitol | 5.00–90.00% |
| Water | 10.00–80.00% |
| Preservatives | 0.01–1.00% |
| Glycerin | 5.00–30.00% |
| Gums/thickeners | 0.500–5.00% |
| Flavors | 0.500–4.00% |
| Buffers | 0.500–5.00% |

In order to prepare the adsorbate suspensions incorporated in the gelatin capsule of the present invention, generally a wet granulation methodology is employed as is known in the art. If magnesium trisilicate is used as the sole adsorbate carrier, it is important to maintain the pH of the process and that of the product as well at a pH of about 8.5 in order to maintain the stability of the trisilicate. If silicon dioxide is employed as the sole adsorbate, pH is of no consequence, but again, this is not preferred. Most preferably a combination of the two is employed wherein pH will not be a major factor of concern. Nevertheless, maintaining a pH as close to 8.5 as possible will produce a better final product.

The soft chewable capsules of the present invention are generally comprised of plasticized gelatin or a pharmaceutically acceptable polymer. The capsule itself is a one-piece, sealed construction enclosing the components therein. Soft capsules are generally used for encapsulating a fluid carrier, a semi-fluid carrier or both. The difficulty in using gelatin as the drug matrix shell is the inherent and marked affinity of the gelatin capsules for water. Usually, special considerations must be taken to keep the water content of the filler material below a critical minimum, otherwise the carrier medium may be adsorbed into the gelatin shell resulting in its degradation and breakdown.

The gelatin capsules are generally comprised of natural or synthetic polymers as is known in the art. Natural gelatin, pectin, casein, collagen, protein, modified starches, polyvinyl pyrolidone and the like are all capsule components well-known in the art. Gelatin is the composition of choice and may be combined with stabilizers, plasticizers and coloring agents as is known in the art. Specific capsules useful in the practice of the present invention and methods for their preparation are described in U.S. Pat. Nos. 4,325,761 and 4,281,763 to Pace, 4,532,126 to Ebert et al. and 4,780,316 to Brox et al., all of which are incorporated by reference.

The filler materials described above may therefore be dispersed in a water immiscible solvent or oil as a carrier medium within the shell. This will also serve as the carrier medium within which the drug adsorbate is dispersed prior to encapsulation.

The gelatin capsule itself is generally ovoid in shape and can be sized according to the potency of the drug and dosage. Other shapes can be utilized according to individual preference although ovoid is generally preferred. Gelatin encapsulation methodologies are well-known in the art, and large scale commercial means are described in U.S. Pat. No. 4,922,682 to Tart et al., U.S. Pat. No. 4,997,359 to Lebrun and Re 33,251 to Wittmer et al., all which are also incorporated by reference.

The following examples are provided to set forth and disclose particular ways of practicing and preparing the novel compositions of the present invention. The are for illustrative purposes only however, and it is understood that minor changes and variations can be made which are not fully contemplated herein. It is to be understood that to the extent any such changes or alterations do not materially affect the final product or process, they are to be considering as falling within the spirit and scope of the invention as recited by the claims that follow.

EXAMPLE I

The following ingredients were collected in their respective amounts in order to prepare the adsorbate suspension of the present invention containing a decongestant/antihistamine dual active therapeutic formulation.

| Ingredient | Percent | Wt/Liter |
| --- | --- | --- |
| 1. POLOXAMER 407 | .3000 | 3.0000 GM |
| 2. POLYETHYLENE GLYCOL 1450 NP | 20.0000 | 200.0000 GM |
| 3. 15% PSEUDOPHENDRINE HYDROCHLORIDE Adsorbate | 4.00 | 40.00 |
| 4. 12% DIPHENYDRAMINE HYDROCHLORIDE Adsorbate | 2.08 | 20.83 |
| 5. SODIUM BENZOATE NF | .4000 | 4.0000 GM |
| 6. SODIUM PHOSPHATE | .02 | 2.00 |
| 7. SODIUM CITRATE GRANULAR USP | .1000 | 1.0000 GM |
| 8. SODIUM CHLORIDE USP GRANULAR (IRON FREE) | .1000 | 1.0000 GM |
| 9. SODIUM SACCHARIN USP GRANULAR | .1000 | 1.0000 GM |
| 10. SORBITOL SOLUTION USP | 60.0000 | 600.0000 GM |
| 11. GLYCERIN USP SPECIAL | 5.0000 | 50.0000 GM |
| 12. MONO AMMONIUM GLYCYRRHIZINATE | .0080 | .0800 GM |
| 13. SODIUM CARBOXYMETHYL CELLULOSE USP TYPE | .2000 | 2.0000 GM |
| 14. 1 RASPBERRY CHERRY FLAVOR ART. NV-17688 (INC) | | |
| 15. 2 D & C RED NO. 33 | .0005 | .0050 GM |
| 16. 3 FD & C RED NO. 40 | .0050 | .0500 GM |
| 17. XANTHAN GUM | 0.8 | 8.0 |
| 18. WATER PURIFIED USP | 100.0000 | 1.0000 L |

The diphenhydramine hydrochloride/pseudoephedrine hydrochloride adsorbate suspension was then prepared as follows. Water (150 ml) was heated in a container with a mixer to 45° C. The Poloxamer 407 was added and mixed until fully dissolved. The polyethylene glycol was then added and the solution mixed for 30 minutes maintaining the temperature at 45° C. A pseudoephedrine hydrochloride adsorbate was previously prepared comprising 15 wt % pseudophendrine HCl, 50 wt % magnesium trisilicate and 35 wt % silicon dioxide. Similarly, a diphenhydramine HCl adsorbate was prepared comprising 12.0 wt % diphenhydramine HCl and 88.0 wt % magnesium trisilicate. Each were then encapsulated within a standard gelatin capsule as is known in the art.

EXAMPLE II

| Ingredient | Weight Percent | gms/kilo |
|---|---|---|
| 1. Diphenhydramine - HCl/Magnesium trisilicate | 3.36 | 33.60 |
| 2. Sorbitol (70% Solution) | 43.07 | 430.07 |
| 3. Xylitol (60% Solution) | 43.07 | 430.07 |
| 4. Xanthan Gum | .35 | 3.5 |
| 5. Sodium Carboxymethyl Cellulose | .15 | 1.5 |
| 6. Glycerin | .10 | 100.0 |

The sorbitol was first mixed with the xylitol to a homogenous blend. to this was added the drug adsorbate followed by further mixing at moderate speed. In a separate container, the sodium carboxymethyl cellulose, glycerin and xanthan gum were mixed well and the two containers were then combined. The suspension was mixed until a smooth, substantially uniform viscous liquid was obtained. A phosphate buffer was added (optional) to raise to pH to about 8.5. The pH was recorded to be 8.38 while the viscosity measured 6750 cps. The suspension was then injected into soft, chewable gelatin capsules as is known in the art. The adsorbate suspension capsules proved stable for extended periods at room temperature, and 30° C., 40° C. and 50° C.

What is claimed is:

1. An oral pharmaceutical delivery system comprising a liquid pharmaceutical suspension for the oral delivery of an unpleasant tasting active agent consisting of a particulate adsorbate with the active medicament contained therein dispersed in an aqueous or non-aqueous carrier solvent encapsulated within a soft, chewable gelatin capsule.

2. The delivery system of claim 1 wherein said adsorbate is selected from the group consisting of magnesium trisilicate, silicon dioxide and mixtures thereof.

3. The delivery system of claim 2 wherein said chewable gelatin capsule is comprised of natural or synthetic polymers and mixtures thereof.

4. The delivery system of claim 3 wherein said chewable capsule further comprises plasticizers, stabilizers, emulsifiers, coloring agents, flavors and mixtures thereof.

5. The delivery system of claim 4 wherein said medicament is selected from the group consisting of antitussives, antihistamines, decongestants, antacids, analgesics, nonsteroidal anti-inflammatory compounds, anti-arrythamtics, antibiotics, anti-convulsants, alkaloids, $H_2$ antagonists, their salts and mixtures thereof.

6. The delivery system of claim 5 wherein said non-aqueous carrier solvent is selected from the group consisting of vegetable oils, fats, mineral oils, paraffin, waxes, fatty acids, sugar alcohols, glycols, glycerin and mixtures thereof.

7. The delivery system of claim 6 wherein said antitussive is selected from the group consisting of dextromethorphan, dextromethorphan hydrobromide, noscapine, carbetapentane, chlorphedianol, their salts and mixtures thereof.

8. The delivery system of claim 6 wherein said antihistamine is selected from the group consisting of chlorpheniramine, phenindamine, pyrilamine, doxylamine, clemastine, brompheniramine, triprolidine, hydroxyzine, meclinzine, cyproheptadine, azatadine, fexofenadine, terfenadine, astemizole, loratadine, cetirizine, phenyltolozamine, triprolidine, their salts and mixtures thereof.

9. The delivery system of claim 6 wherein said decongestant is selected from the group consisting of phenylepherine, phenylpropanolamine, pseudoephedrine hydrochloride, ephedrine, their salts and mixtures thereof.

10. The delivery system of claim 6 wherein said analgesic is selected from the group consisting of acetaminophen.

11. The delivery system of claim 6 wherein said non-steroidal anti-inflammatory is selected from the group consisting of ibuprofen, meclomen, aspirin, indomethicin, oratidine, naproxen, naprosen, astemisol, ketoprofen and mixtures thereof.

12. The delivery system of claim 6 wherein said antibiotic is selected from the group consisting of erythromycin, cephalosporin, tetracycline, penicillin, amoxycillin, clathromycin, their salts and mixtures thereof.

13. The delivery system of claim 6 wherein said $H_2$-antagonist is selected from the group consisting of famotidine, ranitidine, cimetedine, their salts and mixtures thereof.

14. The delivery system of claim 6 wherein said anti-convulsant is selected from the group consisting of phenytoin, ethosuximide, their salts and mixtures thereof.

15. The delivery system of claim 6 further comprising flavorants, sweetening agents, colorants, emulsifiers, stabilizers, thickeners, and mixtures thereof.

* * * * *